United States Patent [19]

Angelucci et al.

[11] Patent Number: 5,773,522
[45] Date of Patent: Jun. 30, 1998

[54] POLYMER-BOUND CAMPTOTHECIN DERIVATIVES

[75] Inventors: Francesco Angelucci; Antonino Suarato, both of Milan, Italy

[73] Assignee: Pharmacia S.p.A., Milan, Italy

[21] Appl. No.: 448,330

[22] PCT Filed: Sep. 21, 1994

[86] PCT No.: PCT/EP94/03154

§ 371 Date: Jun. 8, 1995

§ 102(e) Date: Jun. 8, 1995

[87] PCT Pub. No.: WO95/10304

PCT Pub. Date: Apr. 20, 1995

[30] Foreign Application Priority Data

Oct. 8, 1993 [GB] United Kingdom .................. 9320781

[51] Int. Cl.$^6$ .......................... C08F 20/56; C08F 120/56; C08F 220/56; A01N 43/42
[52] U.S. Cl. .................. 525/329.4; 514/283; 514/81; 546/23; 546/48; 424/280.1
[58] Field of Search .................. 548/100; 514/283, 514/81; 546/1, 23, 26, 48; 435/69.2, 7.23, 233; 424/138.1, 181.1, 277.1, 280.1; 520/573; 525/329.4; 436/64, 106, 813

[56] References Cited

U.S. PATENT DOCUMENTS

| | | | |
|---|---|---|---|
| 4,943,579 | 7/1990 | Vishnujjala et al. | 514/283 |
| 5,362,831 | 11/1994 | Mongelli et al. | |
| 5,473,055 | 12/1995 | Mongelli et al. | |
| 5,569,720 | 10/1996 | Mongelli et al. | |
| 5,571,785 | 11/1996 | Angelucci et al. | |

OTHER PUBLICATIONS

BUNDGAARD. "Design of Prodrugs". Elsevier Science. Chapter 1. pp.1–24, 1985.
Hawkins et al. "New Anticancer Agents: Taxol, Camptothecin Analogs, and Anthrapyrazoles". Oncology. vol. 16, No. 6:17–30, Dec. 1992.
Pommier, Yves. "Eukaryotic DNA Topoisomerase I: Genome Gatekeeper and its Intruders, Camptohecin". Seminars in Oncology. vol. 23, No. 1, Suppl. 3:3–10, Feb. 1996.
Slichenmyer et al. "The Current Status of Camptohecin Analogues as Antitumor Agents". Journal of National Cancer Institute. vol. 85, No. 4:271–291, Feb. 17 1993.
Burke et al. "The Structural Basis of Camptothecin Interactions with Human serum Albumin: Impact on Drug Stability". Journal of Medicinal Chemistry. vol. 37:40–46, 1994.
Hertzberg et al. "On the Mechanism of Topoisomerase I inhibition by Camptothecin: Evidence for Binding to an Enzyme–DNA Complex". Biochemistry. vol. 28:4629–4638, 1989.
Tanizawa et al. "Differential Stabilization of Eukaryotic DNA Topoisomerase I Cleavable Complexes by Camptothecin Derivatives". Biochemistry. vol. 34:7200–7206, 1995.
Eckardt et al. "New Anticancer Agents in Clinical Development". Oncology. vol. 9, No. 11:1191–1199, Nov. 1995.

*Primary Examiner*—Marian C. Knode
*Assistant Examiner*—Datquan Lee
*Attorney, Agent, or Firm*—Oblon, Spivak, McClelland, Maier & Neustadt, P.C.

[57] ABSTRACT

A polymeric conjugate consists essentially of: (i) from 60 to 99 mol % of N-(2-hydroxypropyl) methacryloylamide units represented by formula 1:

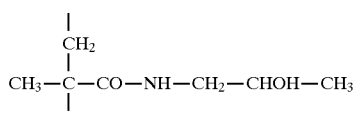

(ii) from 1 to 40 mol % of 20-0-(N-methacryloylglycylaminoacyl) camptothecin units represented by formula 2

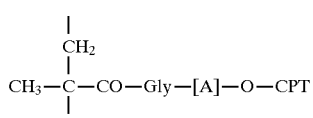

wherein [A] is a spacer group having respective terminal amino and carbonyl groups which are separated by at least three atoms and O-CPT represents a residue of a camptothecin, the C-20 hydroxy group of the camptothecin being linked to the terminal carbonyl group of the spacer group [A]; and (iii) from 0 to 10 mol % of N-methacryloylglycine or N-(2-hydroxy-propyl) methacryloylglycinamide units represented by formula 3:

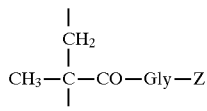

wherein Z represents hydroxy or a residue of formula —NH—CH$_2$—CH(OH)—CH$_3$.

10 Claims, No Drawings

POLYMER-BOUND CAMPTOTHECIN DERIVATIVES

This application is a 371 of PCT/EP94/03154 filed Sep. 21, 1994.

The present invention refers to water soluble polymer-bound camptothecin and polymer-bound camptothecin derivatives endowed with antitumour activity, to a process for their preparation and to pharmaceutical compositions containing them.

Camptothecin is an alkaloid isolated from the leaves and bark of *Camptotheca acuminata;* other analogs of camptothecin are also known and were prepared by semisynthesis from camptothecin or by total synthesis: see J.Amer.Chem.Soc. 94(10), 3631 (1972); J.Chem.Soc.D. (7), 404 (1970); U.S. Pat. No. 4,981,969 (Jan. 1, 1991); U.S. Pat. No. 5,049,668 (Sep.17, 1991).

Camptotnecin has a pentacyclic structure consisting of a fused ring system forming a quinoline ring (rings A and B), a pyrrolidine ring (ring C), a pyridone ring (ring D) and an α-hydroxy-δ-lactone moiety (ring E). Camptothecin and several of its A ring-substituted derivatives exhibit antitumour activity against a variety of solid tumour lines, including cell lines resistant to clinically available chemotherapeutic agents [see: J.Clin.Pharmacol. 30, 770 (1990); Cancer Chemother.Pharmacol. 28, 192 (1991)].

Camptothecin, as well as most of its derivatives, is practically insoluble in vehicles suitable for parenteral administration due to weak basicity of the quinone nitrogen atom. In order to solubilize camptothecins, several water soluble prodrugs have been proposed such as 20-O-phosphate or 20-O-acylamino derivatives which can be protonated by mineral acids, thus allowing solubility: see U.S. Pat. No. 4,943,579 (Jul. 24, 1990). Toxic side effects, including haematological and gastrointestinal ones, are associated with the administration of these drugs. Numerous attempts have been made to improve therapeutic index of camptothecin by modifying its structure.

The present invention provides polymeric conjugates of camptothecins which are water soluble and possess antitumor activity in vivo and decreased toxicity. More particularly, the invention provides a polymeric conjugate which is denoted herein as A and which consists essentially of:

(i) from 60 to 99 mol % of N-(2-hydroxypropyl) methacryloylamide units represented by formula 1:

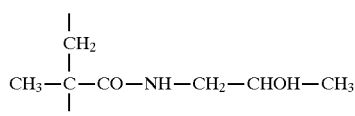

(ii) from 1 to 40 mol % of 20-O-(N-methacryloylglyl aminoacyl)camptothecin units represented by formula 2

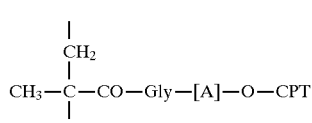

wherein [A] is a spacer group having respective terminal amino and carbonyl groups which are separated by at least three atoms and O-CPT represents a residue of a camptothecin, the C-20 group of the camptothecin being linked to the terminal carbonyl group of the spacer group [A]; and (iii) from 0 to 10 mol % of N-methacryloylglycine or N-(2-hydroxy-propyl) methacryloylglycinamide units represented by formula 3:

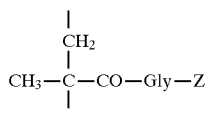

wherein Z represents hydroxy or a residue of formula —NH—CH$_2$—CH(OH)—CH$_3$.

The invention also provides a process for preparing a polymeric conjugate as defined above, which process comprises reacting a 20-O-acylamino-camptothecin derivative of formula 7:

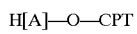

wherein [A] and O-CPT are as defined above, with a polymer consisting essentially of:
(i) from 60 to 99 mol % of N-(2-hydroxypropyl) methacryloyl-amide units represented by formula 1:

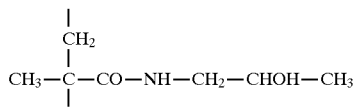

and
(iv) from 40 to 1 mol % of N-methyacryloylglycine units represented by formula 4:

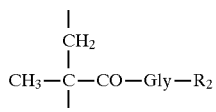

wherein R$_2$ is (a) the residue of an active ester or (b) hydroxy; and optionally displacing the remaining active ester groups with 1-amino-2-propanol.

The polymeric conjugate A contains the N-(2-hydroxypropyl) methacryloylamide units represented by the formula 1 in a proportion of 60 mol % or more, for example at least 80 mol % or at least 85 mol %. These units may be present in an amount from 91 to 98 mol %. The conjugate may also contain from 1 to 40 mol % of the 20-O-(N methacryloylglycyl-aminoacyl)camptothecin units represented by the formula 2, for example from 1 to 20 mol % of such units. The conjugate may contain from 1 to 8 mol %, for example from 2 to 6 mol %, of these units.

The spacer group [8A] may be from three to twelve, for example from six to nine, atoms long. Typically, the group is susceptible to intracellular hydrolysis. Preferably it is resistant to extracelluar hydrolysis. The spacer group may be a peptide spacer, for example from 1 to 4 or 2 to 4 amino acid residues long. The spacer may thus be a dipeptide, peptide or tetrapeptide.

Preferably the spacer group [A] is selected from Ala-Gly, Phe-Gly, Phe-Phe, Leu-Gly, Val-Ala, Phe-Ala, Leu-Phe, Leu-Ala, Phe-Leu-Gly, Phe-Phe-Leu, Leu-Leu-Gly, Phe-Tyr-Ala, Phe-Gly-Phe, Phe-Phe-Gly and Phe-Leu-Gly-Phe. Alternatively the spacer group [A] is a group of formula— HN-Y-CO- in which Y is C$_3$-C$_6$ linear or branched alkyl such as —(CH$_2$)$_n$— wherein n is 3, 4, 5 or 6.

Alternatively, the spacer [A] is a group of formula Ala-Gly-NH-Y-CO-, Phe-Gly-NH-Y-CO-, Phe-Phe-NH-Y-CO-, Leu-Gly-NH-Y-CO-, Val-Ala-NH-Y-CO-, Phe-Ala-NH-Y-CO-, Leu-Phe-NH-Y-CO-, Leu-Ala-NH-Y-CO-, Phe-Leu-Gly-NH-Y-Co-, Phe-Phe-Leu-NH-Y-CO-, Leu-Leu-Gly-NH-Y-CO-, Phe-Tyr-Ala-NH-Y-CO, Phe-Gly-Phe-NH-Y-CO-, Phe-Phe-Gly-NH-Y-CO- or Phe-Leu-Gly-Phe-NH-Y-CO- wherein Y has the same meaning as above.

A residue of a camptothecin is denoted by O-CPT. The camptothecin may be camptothecin itself or an analogue is such as an A-ring analogue. Such an A-ring analogue is thus camptothecin substituted on the A-ring. The camptothecin may be in the natural S form or in the R form or in a mixture of R and S forms (racemic mixture). Suitable camptothecin residues O-CPT are denoted by the formula 5:

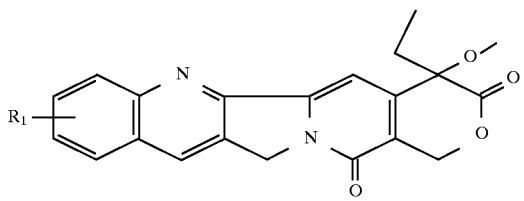
5 wherein $R_1$ represents, for example, hydrogen, hydroxy, nitro or amino or a methylenedioxy group bonded to two adjacent carbon atoms on the A-ring. Preferably $R_1$ represents hydrogen, 9-, 10-, 11- or 12-hydroxy, 9- or 10-nitro, 9- or 10-amino or 10,11-methylenedioxy. More preferred are camptothecin residues of formula 6:

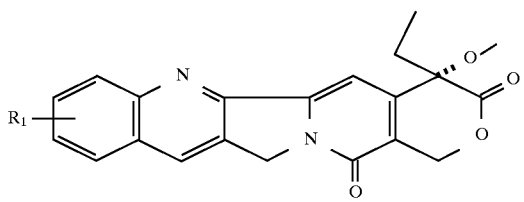
6 wherein $R_1$ is as defined above.

Preferably, the units of formula 2 are present in an amount of from 1 to 10 mol % such as 0.5 to 5 mol %. Also preferably, the camptothecin content is from 1 to 10 % (w/w), more preferably from 4 to 8 % (w/w), based on the polymeric conjugate.

The invention also provides a 20-O-acylamino-camptothecin derivative of formula 7 as defined above. The present invention further provides a process for preparing a 20-O-acylamino-camptothecin derivative of formula 7, which process comprises condensing a camptothecin with a N-protected aminoacyl derivative of formula 8:

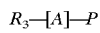
$R_3\text{—[A]—P}$  8 wherein [A] is as defined above and $R_3$ represents an amino-protecting group, such as t-boc, CBZ, FMOC, triphenylsilyl, diphenylmethylene or triphenylmethyl, and P is a residue of an activated ester, such as p-nitrophenoxy, pentafluorophenoxy or N-hydroxysuccinimido, in the presence of an activating agent such as 4-dimethylaminopyridine, to give a N-protected-20-O(acylamino) compound represented by formula 9:

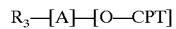
$R_3\text{—[A]—[O—CPT]}$ wherein $R_3$, [A] and [O-CPT] are as defined above; and removing the N-protecting group from the resulting compound.

Preparation of compounds of formula 8 follows standard synthetic procedures that are known from the literature. Suitable N-protected-aminoacyl derivatives of formula 8 include N-trityl-L-phenylalanyl-L-leucyl-glycyl p-nitrophenyl ester (8a) or N-trityl-glycyl-L-leucyl-glycyl p-nitrophenylester (8b), or 6-N-trityl-hexa-noyl p-nitrophenyl ester (8c). Some derivatives of formula 8 and their preparation are described also in our copending International Patent Application No. PCT/EP94/01100.

Thus, for example, a camptothecin may be allowed to react with a molar excess, for example up to a five-fold molar excess or more, especially 2 mol. equivalent, of a N-protected-aminoacyl derivative of formula 5 in anhydrous solvent such as anhydrous dimethylformamide or dimethylsulfoxide in the presence of activating agent such as 4-dimethylaminopyridine. In this manner, the protected amino acid is introduced at position C-20 on the camptothecin molecule. The reaction can typically be effected for from 8 to 24 hours. The reaction is typically carried out at a temperature from 15° to 40° C. It should be noted that, following such reaction conditions, 9-aminocamptothecin regiospecifically reacts at the C-20-hydroxy position due the weak basicity of the 9-amino group.

The amino-protecting group $R_3$ is removed by an appropriate deprotecting agent to give the 20-O-acylamino-camptothecin derivative of formula 7. Deprotection may therefore be achieved by mild acid treatment, such as treatment with acetic acid, or by reduction. Hydrogenolysis may therefore be employed.

The condensation of the 20-O-acylamino-camptothecin derivative of formula 7 with the polymer consisting essentially of from 60 to 99 mol % of the N-(2-hydroxypropyl)-methacryloylamide units of formula 1 and from 40 to 1 mol % of N-methacryloylamide units of formula 4, and the optional subsequent displacement of the remaining active ester groups, are carried out in conditions capable of preserving the nature of linkage between camptothecins and spacers [A] as well as that of the conjugate.

Polymers consisting essentially of from 60 to 99 mol % of the N-(2-hydroxypropyl)-methacryloylamide units of formula 1 and from 40 to 1 mol % of N-methacryloylglycine units of formula 4, are prepared by copolymerization of N-(2-hydroxypropyl)methacrylamide with N-methacryloyl-glycine or N-methacryloylglycine active-ester derivatives, as described in Makromol.Chem. 178, 2159 (1977). $R_2$ may represent a phenyloxy group which is substituted on the phenyl ring by one or more electron-withdrawing groups. Examples of suitable electron-withdrawing groups include nitro ($-NO_2$) and halogen. $R_2$ is preferably the leaving group:

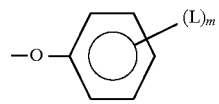

wherein L is an electron withdrawing group, for example $-NO_2$ or a halogen such as fluorine or chlorine, and m is an integer of 1 to 5, typically 1 to 3, preferably 1 or 2. Preferably $R_2$ is a p-nitrophenoxy group or a 2,4-dichlorophenoxy group.

Preferably, the reaction between a polymer in which $R_2$ represents (a) the residue of active ester and a compound of formula 7 to prepare the polymer conjugate of the invention is carried out in an anhydrous polar organic solvent such as dimethyl-formamide or dimethylsulfoxide. The reaction can typically be effected for from 8 to 24 hours. The reaction is typically carried out at temperature from 15° to 30° C., preferably at room temperature for 15 hours; then the aminolysis of the remaining active ester can be performed in the presence of 1-amino-2-propanol at room temperature, for from 0.5 to 1 hour. The conjugate suitably is precipitated with acetone, dissolved in ethanol and reprecipitated with acetone.

In another method, in order to prepare a polymer conjugate of the invention, the reaction between a polymer in which $R_2$ represents hydroxy group (b) and a compound of formula 7 is carried out in an anhydrous polar solvent such as dimethylformamide or dimethylsulfoxide in the presence of a condensing agent such as 2-ethoxy-1-ethoxycarbonyl-1,2-dihydroquinoline. The reaction can typically be effected for from 8 to 24 hours. The reaction is typically carried out at a temperature from 15° to 30° C., preferably at room temperature for 15 hours; then the conjugate can be precipitated with acetone, dissolved in ethanol and reprecipitated with acetone.

For example, the polymer in which $R_2$ represents (a) the residue of an active ester, provided at a concentration of 15% (weight/volume) in anhydrous dimethylsulfoxide, is treated with a 20-O-aminoacyl camptothecin derivative of formula 7, 3% (w/v), at room temperature for 15 hours. Then 1-amino-2-propanol, 0.1% (w/v) is added and the reaction mixture is kept at room temperature for 1 hour. The conjugate can be precipitated with acetone, then dissolved with absolute ethanol at a concentration of 10% (w/v) and precipitated again with acetone to give neutral camptothecin conjugate according to the invention.

In another example, the polymer in which $R_2$ represents (b) hydroxy, provided at a concentration of 15% (weight/volume) in anhydrous dimethylsulfoxide, is treated with a 20-O-aminoacyl camptothecin derivative of formula 7, 3% (w/v), in the presence of 2-ethoxy-1-ethoxycarbonyl-1,2-dihydroquinoline, 1.3% (w/v), at room temperature for 15 hours. Acetone then is added to cause precipitation, the precipitate is dissolved with absolute ethanol at a concentration of 10% (w/v) and precipitation is again caused by acetone addition to give a polymeric conjugate according to the invention.

The content of active drug, such as camptothecin or its A-ring analogues, in polymeric conjugates of the invention is determined by HPLC or absorbance spectroscopy analysis.

Polymer conjugates of camptothecin and its A-ring analogues described in the present invention are endowed with improved water solubility and decreased toxicity. The conjugates exhibit good water solubility, biocompatibility and release camptothecins in the plasma or after internalization into cells by enzymatic cleavage.

Biological Activity

Copolymer of N-(2-hydroxypropyl)methacrylamide, 20-O-[N-methacryloylglycyl -L-phenylalanyl-L-leucylglycyl] camptothecin and N-(2-hydroxypropyl) methacryloylglycinamide (A2) was tested in nude mice transplanted with HT29/Colon Carcinoma (Table 1) and in mice bearing early and advanced M5076 murine reticulosarcoma (Table 2 and 3) in comparison with free camptothecin (CPT).

When compared with camptothecin, a striking higher activity in all experiments was observed for the polymer bound camptothecin derivative A2. It is noteworthy that cured mice were found in the experiment on HT29/Colon Carcinoma.

The antitumor activity was tested with the same treatment schedule for A2 and CPT.

It should be noted that polymer-bound camptothecin A2 and was found highly water soluble and was dissolved in saline and was administered i.v.; whereas CPT was dissolved in a mixture of water and Tween 80.

Drug preparation and administration

Compound A2 was dissolved in distilled water immediately prior to use and the concentration was checked spectrophoto-metrically at 370 nm El % 57.18). Camptothecin (CPT) was dissolved in sterile water with 10% tween.

Treatment was administered i.v. in a volume of 10 ml/kg of body weight and control mice were treated with sterile water.

Tumors

HT29 Colon Carcinoma was transplanted s.c. in athymic Swiss/nu/ mice using 15–20 mg of tumor brei.

M5076 muine reticulosarcoma was maintained by serial i.m. passages and transplanted s.c. ($5 \times 10^5$ cells/mouse) in compatible C57Bl/6 mice.

All animals were from Charles River Calco, Como, Italy.

Ten mice/group for conventional and eight for athymic mice were used.

The conventional mice weighed 20 to 22 g and were kept under standard laboratory conditions.

The mouse colony was routinely tested for the absence of antibodies to a panel of pathogens including Mouse Hepatitis, Sendai Virus and *Mycoplasma Pulmonis*.

Evaluation of antitumor activity and toxicity

Tumor growth was assesed by caliper measurement and the tumor weight estimated according to Geran et al. (see: Cancer Chem.Rep., Part 3, 3 (2) ed. 3, pp 1–103, 1972). The antitumor activity is expressed as percentage of inhibition of tumor growth (%T/I) using the following formula:

$$100 - \frac{\text{(median tumor weight of treated mice)}}{\text{(median tumor weight of control mice)}} \times 100$$

The median increase in survival time (T/C%) was calculated using the following formula:

$$\frac{\text{(median survival time treated mice)}}{\text{(median survival time control mice)}} \times 100$$

Cured mice are mice without tumor at the end of the experiment.

Toxicity was evaluated on the basis of the body weight reduction and gross autopsy findings, mainly in terms of reduction of spleen and liver size.

TABLE 1

Antitumor Activity of Compound A2 in comparison with Camptothecin (CPT) against HT29/Colon Carcinoma.

| Compound | dose[1] mg/kg | treatment schedule | % tumor inhib. | TOX[2] | cured[3] mice |
|---|---|---|---|---|---|
| A2 | 7.5 | iv q4dx6 | 96 | 0/18 | 3/18 |
| CPT | 7.5 | iv q4dx6 | 83 | 0/10 | 0/10 |

[1]expressed as CPT equivalent.
[2]number of toxic deaths/total number of mice
[3]tumor free mice 90 days after tumor implant

TABLE 2

Antitumor Activity of Compound A2 in comparison with Camptothecin (CPT) against early M5076 murine reticulosarcoma.

| Compound | dose[1] mg/kg | treatment schedule | % tumor[3] inhib. | T/C % | TOX[2] |
|---|---|---|---|---|---|
| A2 | 7.5 | iv 1,6,9 | 100 | 171 | 0/10 |
| CPT | 7.5 | ip 1,6,9 | 100 | 165 | 0/10 |

[1] expressed as CPT equivalent.
[2] number of toxic deaths/total number of mice
[3] % tumor inhibition was estimated one week after the last treatment.

TABLE 3

Antitumor Activity of Compound A2 in comparison with Camptothecin (CPT) against advanced M5076 murine reticulosarcoma. Treatment schedule iv on day 16,20,24 28,31,35.

| Compound | Dose[1] mg/kg | % tumor[3] inhibition | T/C % | TOX[2] |
|---|---|---|---|---|
| A2 | 10.0 | 80 | 174 | 0/10 |
|  | 15.0 | 95 | 183 | 0/10 |
| CPT | 7.5 | 72 | 173 | 0/10 |

[1] expressed as CPT equivalent.
[2] number of toxic deaths/total number of mice
[3] % tumor inhibition was estimated at day 34.

Toxicity

Toxicity of copolymer of N-(2-hydroxypropyl)methacrylamide, 20-O-[N-methacryloylglycyl-L-phenylalanyl-L-leucylglycyl] camptothecin and N-(2-hydroxypropyl) methacryloylglycinamide (A2) was evaluated in healthy C57Bl/F mice, treatment i.v. in comparison with camptothecin (CPT).

The $LD_{10}$[1] and $LD_{50}$[2] values in C57B1/F mice are as follows:

| Compound | $LD_{10}$ mg/kg | $LD_{50}$ mg/kg |
|---|---|---|
| A2 | 129 | 151 |
| CPT | 16.9 | 43.4 |

[1] $LD_{10}$: dose inducing 10% of death mice.
[2] $LD_{50}$: dose inducing 50% of death mice.

The low toxicity of polymer-bound camptothecin derivative A2 allows to administer higher doses of product and to reach equivalent or better results than that with camptothecin.

The polymer-bound camptothecins have anti-tumor activity. They inhibit topoisomerase I. They are useful in the treatment of leukaemia and colon and rectal tumors in particular.

A human or animal can therefore be treated by a method comprising administering thereto a therapeutically effective amount of a polymeric conjugate of the invention. The condition of the human or animal patient can thus be improved.

The dosage range adopted will depend on the route of administration and on the age, weight and condition of the patient being treated. The polymeric conjugates are typically administered by the parenteral route, for example intramuscularly, intravenously or by bolus infusion. A suitable dose range is from 1 to 1000 mg of camptothecin equivalent per m² body surface area, for instance from 10 to 50 mg/m².

The polymeric conjugates may be formulated into a pharmaceutical composition together with a pharmaceutically acceptable carrier or diluent. Typically the polymeric conjugates are formulated for parenteral administration, for example by dissolution in water for injection or physiological saline.

The following Examples illustrate the invention without limiting it. Throughout the specification, amino acid residues are shown in the three-letter code according to Eur.J-.Biochem. 138, 9–37, 1984.

Stability of polymeric conjugates in murine or human plasma was assessed in the following manner: to 1 ml of murine or human plasmas, various concentrations of a polymeric conjugate of the invention A were added and at appropriate time (24, 48, 72, 96 hours) 100 µl samples were collected and stored at −70° C. until further processing.

Each sample was extracted by adding 100 µl of 0.25M phosphoric acid, 500 µl $CH_3CN$ and 700 µl ethyl acetate and vigorously shaking for 20 minutes at 4° C. After that time, the sample was spun at 15000×g for 10 minutes and the supernatant was separated. To the residue was added 300 µl of $CH_3CN$ and 500 µl was spun at 15000×g for 10 minutes. The supernatant was separated. The organic phases were pooled and evaporated using a high vacuum centrifuge. The sample was recovered by adding 500 µl of MeOH/water pH2 (70/30 by volume) and injected into HPLC apparatus for determining the total drug percentage content.

| HPLC system | |
|---|---|
| Column | µBondapak C10 (Waters) 3.9 × 300 mm |
| Flow rate | 1.5 ml/min |
| Detector | Spectrophotometer Fluorescence 650-40 (Perkin Elmer); emission 434 nm (slit 5); excitation 370 nm (slit 5) |
| Injection | 10 µl |
| Mobile Phase | 51.5% MeOH, 47.5% water, 1% phosphoric acid |

Example 1

6-N-tritvl-hexanoyl p-nitrophenyl ester (8c)

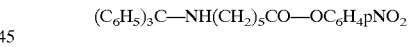

$(C_6H_5)_3C$—$NH(CH_2)_5CO$—$OC_6H_4pNO_2$      8c

6-Aminocaproic acid (6.5 g, 50 mmol) suspended in a mixture of dry chloroform (75 ml) and dry acetonitrile (15 ml) was added with trimethylsilyl chloride (6.3 ml, 50 mmol) and kept under reflux for two hours under vigorous stirring. After that, the mixture was cooled and added in sequence were triethylamine (13.7 ml, 100 mmol) and trityl chloride (14 g, 50 mmol) dissolved in dry chloroform (100 ml). The mixture was let to stand overnight at room temperature, then methanol (10 ml) was added and the reaction mixture was concentrated under reduced pressure. The residue was picked up with cold aqueous 5% citric acid (200 ml) and extracted with ethyl acetate (200 ml). The organic phase was separated and extracted with cold aqueous 1N sodium hydroxide (200ml). The aqueous phase was separated, cooled with ice, brought to pH 5 with acetic acid and extracted with ethyl acetate (2×100 ml). The organic solvent was removed under reduced pressure to afford, after crystallization from ethyl acetate, 6-N-trityl-hexanoic acid (16 g). This material was dissolved in anhydrous tetrahydrofurane (150 ml) and treated with p-nitrophenol (5.6 g, 400 mmol) and dicyclohexylcarbodiimide (8.4 g, 40 mmol) at 0° C. for one hour under stirring, then overnight at 8° C.

After that, the reaction mixture was filtered, cooled at 0° C. for two hours and filtered again. Finally, the organic solvent was removed under reduced pressure and the residue was crystallized with ethyl ether to afford the title compound 8c (16.4 g). TLC on Kieselgel plates $F_{245}$, (Merck), eluting system ethyl ether/n-hexane (1:1 by volume) $R_f$=0.6; FD-MS: m/z [M+H]$^+$495 $^1$HNMR (90 MHz, CDCl$_3$) δ: 1.1–1.9 (m, 6H); 2–2.5 (m, 4H); 5.7–5.9 (m, 2H, NH, —COOH); 7.2–7.7 (m, 15 H).

Example 2

20-O-(6-aminohexanoyl)camptothecin (7a)

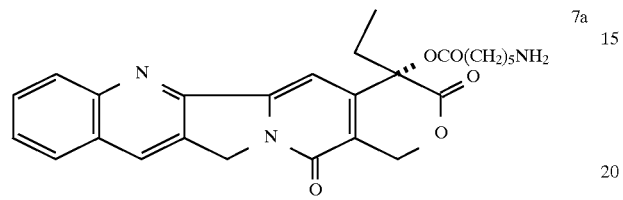

Camptothecin (6a, R$_1$=H, 0.7 g, 2 mmol) was dissolved in dry dimethylsulfoxide (100 ml) and added with 6-N-trityl-hexanoyl p-nitrophenyl ester (8c, 2 g, 4 mmol), prepared as described in Example 1, and 4-dimethylaminopyridine (0.24 g, 2 mmol). The reaction mixture was kept at room temperature for 48 hours, then diluted with chloroform (400 ml) and washed with water (3×100 ml). The organic phase was separated, dried over anhydrous sodium sulphate and concentrated to small volume under reduced pressure. The crude material was flash chromatographed on silicic acid column eluting with chloroform to afford 20-O-(6-N-tritylhexanoyl)camptothecin (0.6 g). TLC on Kieselgel plates $F_{245}$ (Merck), eluting system chloroform/methanol (95:5 by volume) $R_f$=0.4. The N-protected derivative was treated with 95% trifluoroacetic acid (10 ml) at room temperature for 50 minutes. After removal of the acid under reduced pressure, the title compound 7c was collected with ethyl ether. Yield 0.4 g. TLC on Kieselgel plates $F_{245}$ (Merck), eluting system methylene chloride/methanol/acetic acid/water (80:20:7:3) $R_f$=0.6. FD-MS: m/z [M+H]$^+$462

Example 3

20-O-(L-Phenylalanyl-L-Leucyl-Glycl)camptothecin (7b)

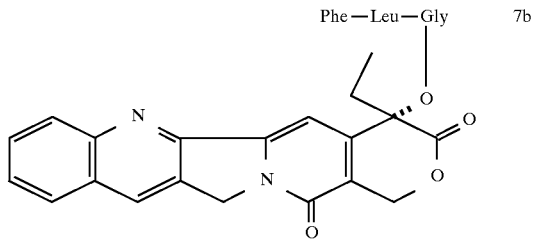

N-trityl-L-phenylalanyl-L-leucylglycine p-nitrophenyl ester (8a, 1.4 g, 2 mmol) prepared as previously described in UK Application No. 9309663.4, camptothecin (6a, R$_1$=H, 0.35 g, 1 mmol) and 4-dimethylaminopyridine (0.12 g, 1 mmol) were dissolved with dry dimethylsulfoxide (50 ml) and stirred at room temperature for 20 hours. After that, the reaction mixture was diluted with chloroform (400 ml) and washed with water (3×100 ml). The organic phase was separated, dried over anhydrous sodium sulphate and concentrated to small volume under reduced pressure. The crude material was flash chromatographed on silicic acid column eluting with a mixture of chloroform/methanol (99.5/0.5 by volume). The fractions containing the N-protected derivative of the title compound were pooled, concentrated to dryness, dissolved with aqueous 75% acetic acid (30 ml) and kept at room temperature for one hour. The reaction mixture was treated wtih solid sodium hydrogen carbonate to pH 7 and extracted with chloroform (400 ml). After removal of the organic solvent, the title compound 7b was crystallized from ethyl ether. Yield 0.16 g. TCL on Kieselgel plates $F_{245}$ (Merck), eluting system chloroform/methanol (9:1 by volume) $R_f$0.35

FD-MS:m/z [M+H]$^+$667

$^1$H-NMR (400 MHz,CDCl$_3$) δ:

0.81 (d, J=6.5Hz, 3H, δ-Leu); 0.82 (d, J=6.6 Hz, 3H, δ'-Leu);

0.98 (t, J=7.6 Hz, 3H, CH$_3$–CH$_2$); 1.25 (m, 1H, β-Leu); 1.39 (m, 1H, —Leu); 1.56 (m, 1H, β'-Leu); 1.98 (dd, J=6.4 Hz, J=13.5 Hz, 1H, β-Phe); 2.1–2.4 (m, 2H, CH$_2$CH$_3$); 2.48 (d, J=7.0 Hz, 1H, NH-Phe); 2.77 (dd, J=4.7 Hz, J=13.5 Hz, 1H, β'-Phe); 3.41 (m, 1H, α-Phe); 4.0–4.3 (m, 3H, α-Gly+α'-Gly+α-Leu); 5.20–5.27 (two-d, J=19.9 Hz, 2H, 5—CH$_2$); 5.41–5.68 (two-d, J=17.3 Hz, 2H, 17—CH$_2$); 6.35 (t, J=5.3 Hz, 1H, NH-Gly);

6.76 (d, J=7.6Hz, 1H, NH-Leu); 6.8–7.3 (m, 21H, 4×(C$_6$H$_5$)+14—H).

Example 4

9-amino-20-O-(L-Phenylalanyl-L-Leucyl-Glycyl camptothecin (7c)

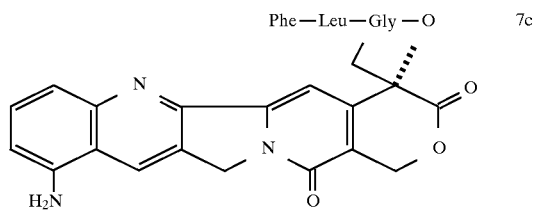

N-trity-L-phenylalanyl-L-leucylglycine p-nitrophenyl ester (8a, 1.14 g, 2 mmol), 9-amino-camptothecin (6b, R$_1$=NH$_2$, 0.363 g, 1 mmol), 4-dimethylaminopyridine (0.12 g, 1 mmol) were reacted in dry dimethylsulfoxide (20 ml) at room temperature as described in Example 3 to give the title compound 7c (0.31 g). TLC on Kieselgel plates $F_{245}$ (Merck), eluting system chloroform/methanol (9:1 by volume) $R_f$=0.2 FD-MS: m/z *[M+H]$^+$682; $^1$H-NMR (400 MHz, CDCl$_3$) δ: 0.82 (d, J=6.5 Hz, 6H, δ-Leu+δ'-Leu); 1.00 (t, J=7.6 Hz, 3H, CH$_2$CH$_3$); 1.25 (m, 1H, δ-Leu); 1.41 (m, 1H, -Leu); 1.59 (m, 1H, β'-Leu); 1.99 (dd, J=6.2 Hz, J=13.5 Hz, 1H, βPhe); 2.1–2.4 (m, 2H, CH$_2$CH$_3$); 2.47 (d, J=6.5 Hz, 1H, NH-Phe); 2.79 (dd, J=4.7 Hz, J=13.5 Hz, 1H, β'-Phe); 3.43 (m, 1H, α-Phe); 4.0–4.3 (m, 5H, 9-NH$_2$+α-Leu+α-Gly+α'-Gly); 5.04–5.15 (two-d, J=19.9Hz, 2H, CH$_2$); 5.39–5.66 (two-d, J=17.0 Hz, 2H, 17-CH$_2$); 6.44 (t, J=5.3 Hz, 1H, NH-Gly); 6.81 (d, J=7.6Hz, 1H, NH-Leu); 6.85 (m, 3H, 10—H +

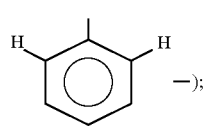
—);

7.0–7.4 (m, 19H, 3×C$_6$H$_5$

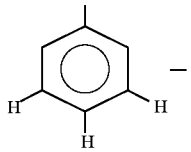

+14—H); 7.51 (m, 1H, 11—H).

Example 5

Copolymer of N-(2-hydroxypropyl)methacrylamide, 20-O-[N-methacryloylglycyl-(6-aminohexanoylyl] camptothecin and N-(2-hydroxy-propyl)methacryloylglycinamide (A1:x=96, , y=3, , z=1)

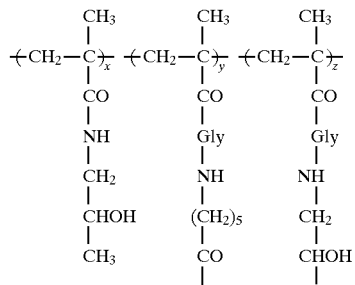

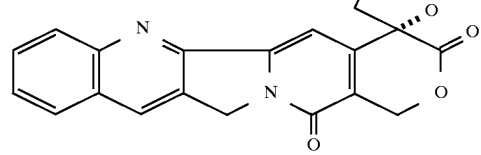

Copolymer of N-(2-hydroxypropyl)methacrylamide and N-methacryloylglycine p-nitrophenylester (0.15 g), prepared as described in Makromol.Chem., 178, 2159 (1977), containing 2.7×10$^3$ equivalents of p-nitrophenylester, was reacted with 20-O-(6-aminohexanoyl)camptothecin (7c, 18 mg), prepared as described in Example 2, in dry dimethylsulfoxide (1 ml) at room temperature for 18 hours, then with 1-amino-2-propanol (2 μl) for one hour at room temperature. After that, the reaction mixture was treated with acetone (70 ml). The precipitate was collected, redissolved with anhydrous ethanol (5 ml) and reprecipitated with acetone (50 ml) to give the title conjugate A1 (0.14 g) containing 5% (w/w) of camptothecin. After plasma incubation, conjugate A1 releases 10% of camptothecin after 120 hours.

Example 6 copolymer of N-(2-hydroxypropyl)methacrylamide, 20-O-[N-metha -cryloylglycyl-L-phenylalanyl-L-leucylalycyl]camptothecin and N-(2-hydroxypropyl)methacryloylglycinamide (AP:x=96, y=2.2, z=1.8)

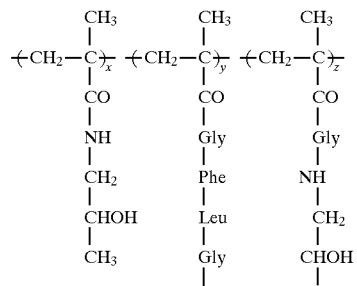

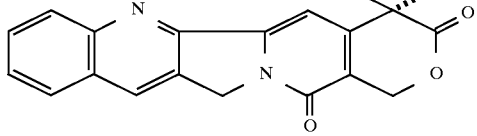

Copolymer of N-(2-hydroxypropyl)methylacrylamide and N-N-methacryloylglycine p-nitrophenylester (0.15 g), containing 2.7×10$^3$ equivalents of p-nitrophenylester) and 20-O-(Glycyl-L-leucyl-L -phenylalanyl)camptothecin (7b, 20 mg), prepared as described in Example 3 were reacted in dry dimethylsulfoxide (1 ml), then with 1-amino-2-propanol as described in Example 6 to give the title conjugate A2 (0.14 g), containing 4.8% w/w of camptothecin. After plasma incubation, conjugate A2 released 100% of camptothecin after 60 hours.

Example 7

Copolymer of N-($^2$-hydroxypropyl)methacrylamide) 9-amino-20-O-[N-methacryloylglycyl-L-phenylalanyl-L-leucylglycyl] campto-thecin and N-(2-hydroxypropyl)methacryloylalycinamide (A3:x=96, y=3, z=1)

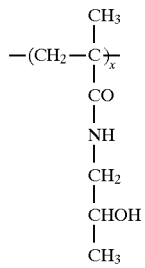

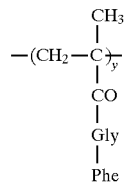

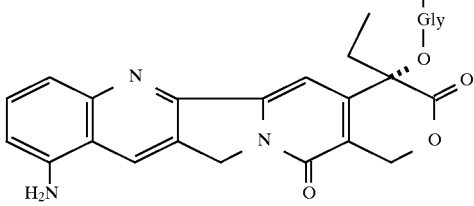

-continued $$-(CH_2-\underset{\underset{\underset{\underset{CH_3}{|}}{CHOH}}{\underset{|}{CH_2}}}{\overset{\overset{CH_3}{|}}{\underset{|}{C}}})_{\overline{z}}$$

The title conjugate was prepared by reacting copolymer of N-(2-hydroxypropyl) methacrylamide and N-methacryloylglycine p-nitrophenylester (0.15 g, containing $2.7 \times 10^{-3}$ equivalents of p-nitrophenylester) and 9-amino-20-O-(Glycyl-L-leucyl-L-phenylalanyl) camptothecin (7c, 20 mg), prepared as described in Example 4 in dry dimethylsulfoxide (1 ml), then with 1–35-amino-2-propanol as described in Example 5. Yield 0.14 g, containing 6.3% w/w of 9-amino-camptothecin. After plasma incubation, conjugate A3 releases 100% of camptothecin after 50 hours.

We claim:

1. A polymeric conjugate which consists essentially of:
   (i) from 60 to 99 mol % of N-(2-hydroxypropyl) methacryloylamide units of formula 1:

$$\underset{\underset{|}{CH_3-\underset{|}{C}-CO-NH-CH_2-CHOH-CH_3}}{\overset{\overset{|}{CH_2}}{|}} \quad (1)$$

(ii) from 1 to 40 mol % of 20-O-(N-methacryloylglycylaminoacyl)camptothecin units of formula 2

$$\underset{\underset{|}{CH_3-\underset{|}{C}-CO-Gly-CH_2-[A]-O-CPT}}{\overset{\overset{|}{CH_2}}{|}} \quad (2)$$

wherein is a spacer group having respective terminal amino and carbonyl groups which are separated by at least three atoms and O-CPT is a camptothecin, the C-20 hydroxy group of the camptothecin being linked to the terminal carbonyl group of the spacer group; and
   (iii) from 0 to 10 mol % of N-methylacryloylglycine or N-(2-hydroxy-propyl)methacryloylglycinamide units of formula 3:

$$\underset{\underset{|}{CH_3-\underset{|}{C}-CO-Gly-Z}}{\overset{\overset{|}{CH_2}}{|}} \quad (3)$$

wherein Z is hydroxy or a radical of the formula —NH—CH$_2$—CH(OH)—CH$_3$.

2. The conjugate according to claim 1, wherein the spacer group is selected from the group consisting of Ala-Gly, Phe-Gly, Phe-Phe, Leu-Gly, Val-Ala, Phe-Ala, Leu-Phe, Leu-Ala, Phe-Leu-Gly, Phe-Phe-Leu, Leu-Leu-Gly, Phe-Tyr-Ala, Phe-Gly-Phe, Phe-Phe-Gly and Phe-Leu-Gly-Phe.

3. The conjugate according to claim 1, wherein the spacer group has the formula —UN—Y—CO— wherein Y is a $C_3$–$C_6$ linear or branched alkyl group or Ala-Gly-NH-Y-CO-, Phe-Gly-NH-Y-CO-, Phe-Phe-NH-Y-CO-, Leu-Gly-NH-Y-CO-, Val-Ala-NH-Y-CO-, Phe-Ala-NH-Y-CO-, Leu-Phe-NH-Y-CO-, Leu-Ala-NH-Y-CO-, Phe-Leu-Gly-NH-Y-CO-, Phe-Phe-Leu-NH-Y-CO, Phe-Phe-Leu-NH-Y-CO-, Leu-Leu-Gly-NH-Y-CO-, Phe-Tyr-Ala-NH-Y-CO, Phe-Gly-Phe-NH-Y-CO-, Phe-Phe-Gly-NH-Y-CO-, or Phe-Leu-Gly-Phe-NH-Y-CO-.

4. The conjugate according to claim 1, wherein O-CPT is a camptothecin of formula 6:

(6)

wherein $R_1$ is hydrogen, hydroxy, nitro or amino or a methylenedioxy group bonded to two adjacent carbon atoms on the A-ring.

5. The conjugate according to claim 1, wherein from 1 to 10 mol % of the said units of formula 2 are present.

6. A conjugate according to claim 1, wherein the camptothecin content is from 1 to 10% (w/w).

7. A process for preparing a polymeric conjugate which consists essentially of:
   (i) from 60 to 99 mol% of N-(2-hydroxypropyl) methacryloylamide units of formula 1:

$$\underset{\underset{|}{CH_3-\underset{|}{C}-CO-NH-CH_2-CHOH-CH_3}}{\overset{\overset{|}{CH_2}}{|}} \quad (1)$$

(ii) from 1 to 40 mol % of 20-O-(N-methacryloylglycylaminoacyl)camptothecin units of formula 2

$$\underset{\underset{|}{CH_3-\underset{|}{C}-CO-Gly-CH_2-[A]-O-CPT}}{\overset{\overset{|}{CH_2}}{|}} \quad (2)$$

wherein is a spacer group having respective terminal amino and carbonyl groups which are separated by at least three atoms and O-CPT is a camptothecin, the C-20 hydroxy group of the camptothecin being linked to the terminal carbonyl group of the spacer group; and
   (iii) from 0 to 10 mol % of N-methylacryloylglycine or N-(2-hydroxy-propyl) methacryloylglycinamide units of formula 3:

$$\underset{\underset{|}{CH_3-\underset{|}{C}-CO-Gly-Z}}{\overset{\overset{|}{CH_2}}{|}} \quad (3)$$

wherein Z is hydroxy or a radical of the formula —NH—CH$_2$—CH(OH)—CH$_3$, which process comprises reacting a 20-O-acylamino-camptothecin of formula 7:

$$H-[A]-O-CPT \quad (7)$$

with a polymer consisting essentially of:

(iv) from 60 to 99 mol % of N-(2-hydroxypropyl) methacryloylamide units of formula 1:

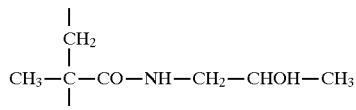 (1)

and (v) from 40 to 1 mol % of N-methyacryloylglycine units of formula 4:

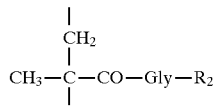 (4)

wherein $R_2$ is an active ester or (b) hydroxy; and optionally displacing the remaining active ester groups with 1-amino-2-propanol.

8. A 20-O-acylamino-camptothecin of formula 7:

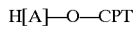 (7)

wherein is a spacer group having respective terminal amino and carbonyl groups which are separated by at least three atoms and O-CPT is a camptothecin, the C—20 hydroxy group of the camptothecin being linked to the terminal carbonyl group of the spacer group.

9. A process for preparing the 20-O-acylamino-camptothecin of formula 7:

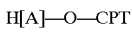 (7)

wherein is a spacer group having respective terminal amino and carbonyl groups which are separated by at least three atoms and O-CPT is a camptothecin, the C—20 hydroxy group of the camptothecin being linked to the terminal carbonyl group of the spacer group comprising the steps of:

condensing a camptothecin with a N-protected-aminoacyl derivative of the formula 8:

 (8)

wherein is as above defined, $R_3$ is an amino-protecting group and P is an activated ester, in the presence of an activating agent to give a N-protected 20-O-(acylamino) compound having formula 9:

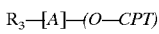 (9)

wherein $R_3$ and are as defined above and O-CPT is a camptothecin, the C—20 hydroxy group of the camptothecin being linked to the terminal carbonyl group of the spacer group; and removing the N-protecting group from the resulting compound.

10. A pharmaceutical composition comprising a pharmaceutically acceptable diluent or carrier, and as active ingredient, a polymeric conjugate as claimed in claim 1.

* * * * *